United States Patent [19]

Miyazawa et al.

[11] Patent Number: 5,449,793
[45] Date of Patent: Sep. 12, 1995

[54] PROCESS FOR PRODUCING AN OPTICALLY ACTIVE 1,5-DISUBSTITUTED-2,4-O-ISOPROPYLIDENE-2,4-DIHYDROXYPENTANE

[75] Inventors: Kazutoshi Miyazawa; Teruyo Sugiura; Yasuyuki Koizumi, all of Ichiharashi; Naoyuki Yoshida, Chibaken, all of Japan

[73] Assignee: Chisso Corporation, Osaka, Japan

[21] Appl. No.: 241,994

[22] Filed: May 12, 1994

Related U.S. Application Data

[62] Division of Ser. No. 70,985, Jun. 4, 1993, Pat. No. 5,329,018.

[51] Int. Cl.$^6$ .......................................... C07D 319/06
[52] U.S. Cl. ................................... 549/373; 549/374; 549/375; 560/239
[58] Field of Search ..................... 549/373, 374, 375; 560/239

[56] References Cited

PUBLICATIONS

*J. Org. Chem.*, 58, No. 4, (1993), pp. 802 and 803, Carlo Bonini et al.
*Acc. Chem. Res.*, 23, (1990), pp. 114–118, A. M. Klibanov.
*Chem. Pharm. Bull.*, 37, No. 6, (1989), pp. 1650–1652, Zhuo–Feng Xie et al.
*J. Org. Chem.*, 57, No. 5, (1992), pp. 1559–1563, Scott D. Rychnovsky et al.
*Tetrahedron Letters*, 33, No. 23, (1992), pp. 4183–4186, Hirokazu Urabe et al.
Chemical Abstract, vol. 75, No. 5, 36533p, Kuszmann et al., (1971), p. 558.
Chemical Abstract, vol. 70, No. 13, 58187c, Zarubinskii et al., (1969), p. 416.
Chemical Abstract, vol. 91, No. 11, 91886m, Horvath et al., (1979), p. 805.

*Primary Examiner*—C. Warren Ivy
*Assistant Examiner*—Ba K. Trinh
*Attorney, Agent, or Firm*—Leydig, Voit & Mayer

[57] ABSTRACT

A novel optically active erythro-1-alkanoyloxy-2,4-O-isopropylidene-2,4-dihydroxy-5-substituted pentane expressed by the formula

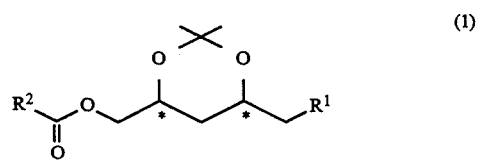

(1)

wherein $R^1$ represents a halogen atom or cyano group and $R^2$ represents an alkyl group of 1 to 6 carbon atoms, and a process for producing the above compound are provided, the compound being preferably usable as an intermediate for preparing a HMG-CoA reductase inhibitor and the process being practiced under mild conditions and with a high yield.

23 Claims, No Drawings

PROCESS FOR PRODUCING AN OPTICALLY ACTIVE 1,5-DISUBSTITUTED-2,4-O-ISOPROPYLIDENE-2,4-DIHYDROXYPENTANE

This application is a divisional of application Ser. No. 08/070,985, filed Jun. 4, 1993, now U.S. Pat. No. 5,329,018.

BACKGROUND OF THE INVENTION

1. Field of the Invention

This invention relates to a method of producing a novel optically activate substance, preferably usable as an intermediate for preparing HMG-CoA reductase inhibitor, known as a remedy for high cholesterol blood disease.

2. Description of the Related Art

The HMG-CoA reductase inhibitor has been noted as a remedy for high cholesterol blood disease, and a number of its homologues have been synthesized and active research of its pharmaceutical activity has been carried out. As one area of research, a pyrrole derivative of the following formula (7) has been disclosed in U.S. Pat. No. 4,681,893 (Bruce D. Roth et al):

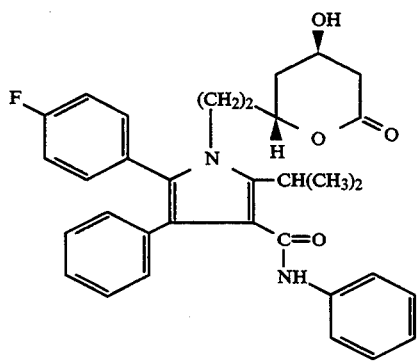

(7)

Further, an effective process for producing the compound of the formula (7) has been disclosed in U.S. Pat. No. 5,003,080 (Donald E. Butler et al). The literature of the prior art shows that when the following compounds of the formulas (8) and (9) are treated with 10% hydrochloric acid, the compound of the formula (7) can be easily prepared:

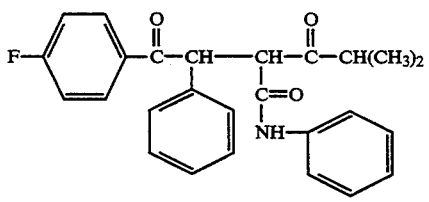

(8)

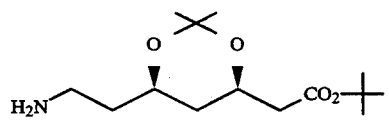

(9)

Further, it is also shown that the other preparation fragment (9) is prepared by catalytically reducing the following nitrile compound (10) at 0° to 70° C.:

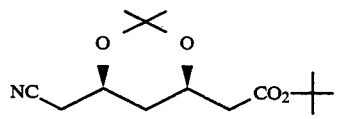

(10)

However, the process for producing the nitrile compound (10), disclosed in the above literature of the prior art is commercially inferior. Namely, the disclosed process for producing the nitrile compound (10) consists of the following steps:

Firstly, an alkyllithium, iodine and $CO_2$ in this order are reacted with 1,6-heptadiene-4-ol (11) to generate an iodide (12) in the reaction system, followed by treating it with an alkali or alkaline earth hydroxide or carbonate to prepare an epoxide (13).

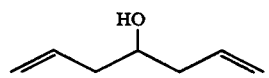

(11)

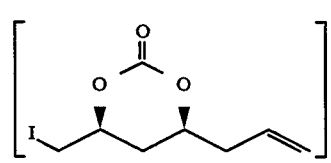

(12)

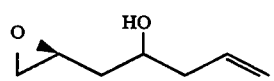

(13)

An alkali metal cyanide is reacted with the epoxide to open the oxirane ring, followed by ketalization to obtain (14), oxidizing it with ozone at −20° to −78° C. to obtain an aldehyde (15), further oxidizing it with Jones reagent to obtain a carboxylic acid (16), and esterifying it with an alkyl halide in the presence of 1,8-diazabicyclo[5,4,0]-7-undecene (DBU) to obtain (17).

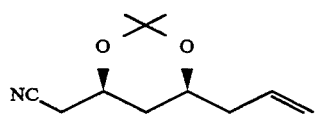

(14)

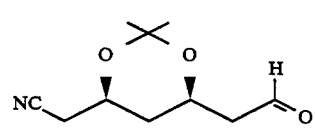

(15)

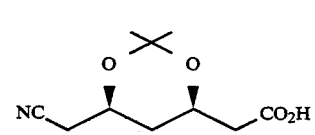

(16)

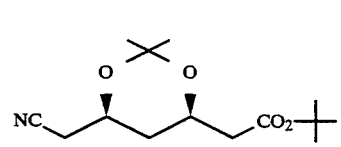

(17)

However, the above processes have the following commercial disadvantages:

1. In the preparation of (12), it is necessary to use an alkyllithium which is difficult to deal with.

2. In the preparation of (15), it is necessary to carry out ozone oxidation at low temperatures (−20° to −78 ° C.).

3. In the preparation of (16), it is necessary to use Jones reagent containing harmful chromic acid.

Furthermore, according to this preparation route, while it is possible to separately prepare an erythro-form substance and a threo-form substance, it is impossible to prepare an optically active substance. Thus, the final product prepared through the preparation route is a racemic substance. A pyrrole derivative having a physiological activity as HMG-CoA reductase inhibitor is only 2R-transform substance expressed by the formula (7), and optical isomers have no activity.

The above U.S. Pat. No. 5,003,080 also discloses preparation of an optically active substance. Namely, the above optically active nitrile compound (10) is prepared through the following route:

A carboxylic acid (19) derived from isoascorbic acid (18) according to a known method has one more carbon atom increased, using carbonyldiimidazole and a half ester of malonic acid, to prepare (20), followed by removing the protective group to obtain an alcohol (21).

This alcohol is stereoselectively reduced with triethylborane or methoxydiethylborane and then with sodium borohydride, at −78° to −110° C., preferably −100° C., to obtain a diol (22), followed by protecting the hydroxyl groups with acetonide to obtain the above nitrile compound (10).

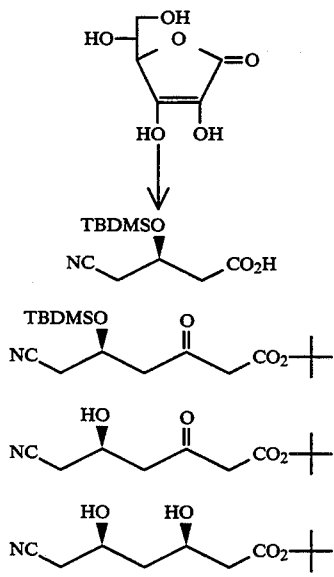

However, the above process cannot be regarded as a commercially advantageous process, since conversion of the isoascorbic acid (18) into the carboxylic acid (19) requires a number of steps and reduction of the alcohol (21) requires an extremely low temperature (because no stereoselectivity is exhibited at high temperatures). Thus, a novel optically active compound equivalent to optically active nitrile compound (10) or easily convertible into (10), and a process for producing a novel optically active compound easily convertible into (10) under mild reaction conditions and commercially advantageously, have been required.

The present inventors have made extensive research in order to solve the above-mentioned problems, and as a result, have found a novel and useful optically active compound, i.e. an optically active erythro-1-alkanoyloxy-2,4-O-isopropylidene-2,4-dihydroxy-5-substituted pentane (1) of the present invention, equivalent to or easily converted into an optically active nitrile compound (10) as a raw material for preparing a pyrrole derivative (7) which is one of HMG-CoA reductase inhibitors, and a suitable and simple process for producing the compound of the present invention (1); thus the present invention has been completed.

As apparent from the foregoing, the object of the present invention is to provide the above-mentioned novel compound and a process for producing the same.

SUMMARY OF THE INVENTION

The present invention has the following constitutions:

An optically active erythro-1-alkanoyloxy-2,4-O-isopropylidene-2,4-dihydroxy-5-substituted pentane expressed by the formula

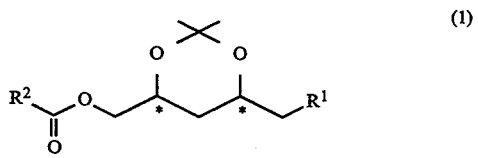

wherein $R^1$ represents a halogen atom or cyano group and $R^2$ represents an alkyl group of 1 to 6 carbon atoms.

2. A process for producing an optically active erythro-1-alkanoyloxy-2,4-O-isopropylidene-2,4-dihydroxy-5-halogenopentane, which process comprises reacting an ester with meso-1,2,4,5-pentanetetraol expressed by the formula

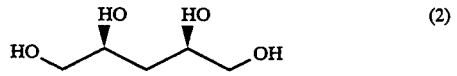

in the presence of a lipase to prepare a meso-1,5-alkanoyloxy-2,4-dihydroxypentane expressed by the formula

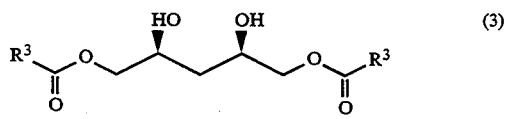

wherein $R^3$ represents an alkyl group of 1 to 10 carbon atoms;

ketalizing the compound (3) to prepare a meso-1,5-dialkanoyloxy-2,4-O-isopropylidene-2,4-dihydroxypentane expressed by the formula

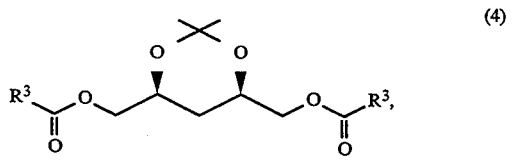

dealkanolizing the compound (4) to prepare meso-2,4-O-isopropylidene-1,2,4,5-pentane tetraol expressed by the formula

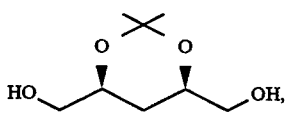

reacting an ester with (5) in the presence of a lipase to prepare an optically active erythro-1-alkanoyloxy-2,4-O-isopropylidene-1,2,5-pentanetriol expressed by the formula

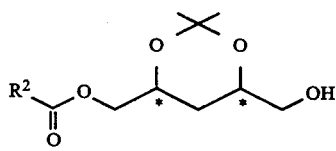

wherein $R^2$ represents an alkyl group of 1 to 6 carbon atoms, and halogenating it, to prepare an optically active erythro-1-alkanoyloxy-2,4-O-isopropylidene-2,4-dihydroxy-5-halogenopentane expressed by the formula

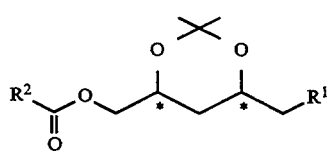

wherein $R^1$ represents a halogen atom and $R^2$ represents an alkyl group of 1 to 6 carbon atoms.

3. A process for producing an optically active erythro-1-alkanoyloxy-2,4-O-isopropylidene-2,4-dihydroxy-5-cyanopentane, which process comprises reacting an ester with, meso-1,2,4,5-pentanetetraol expressed by the formula

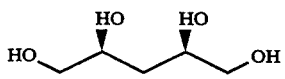

in the presence of a lipase to prepare a meso-1,5-alkanoyloxy-2,4-dihydroxypentane expressed by the formula

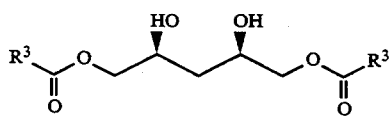

wherein $R^3$ represents an alkyl group of 1 to 10 carbon atoms;

ketalizing the compound (3) to prepare a meso-1,5-dialkanoyloxy-2,4-O-isopropylidene-2,4-dihydroxypentane expressed by the formula

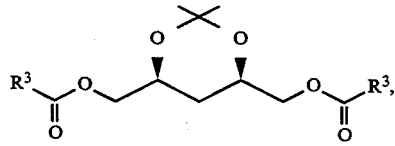

dealkanolizing the compound (4) to prepare meso-2,4-O-isopropylidene-1,2,4,5-pentane tetraol expressed by the formula

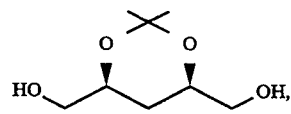

reacting an ester with (5) in the presence of a lipase to prepare an optically active erythro-1-alkanoyloxy-2,4-O-isopropylidene-1,2,5-pentanetriol expressed by the formula

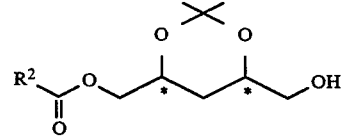

wherein $R^2$ represents an alkyl group of 1 to 10 carbon atoms, halogenating it, to prepare an optically active alkanoyloxy-2,4-O-isopropylidene-2,4-dihydroxy-5-halogenopentane expressed by the formula

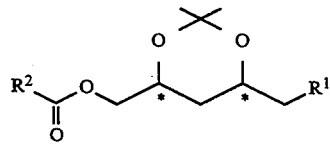

wherein $R^1$ represents a halogen atom and $R^2$ represents an alkyl group of 1 to 6 carbon atoms, and cyanizing it, to prepare an optically active erythro-1-alkanoyloxy-2,4-O-isopropylidene-2,4-dihydroxy-5-cyanopentane expressed by the formula

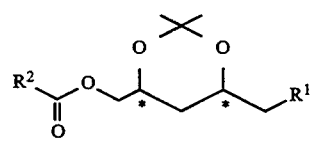

wherein $R^1$ represents a cyano group and $R^2$ represents an alkyl group of 1 to 6 carbon atoms.

4. A process for producing an optically active erythro-1-alkanoyloxy-2,4-O-isopropylidene-1,2,5-pentanetriol expressed by the formula

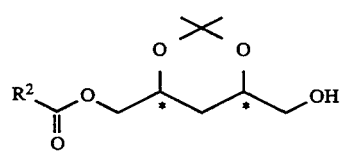

wherein $R^2$ represents an alkyl group of 1 to 6 carbon atoms, which process comprises reacting an ester with meso-2,4-O-isopropylidene-1,2,4,5-pentanetetraol expressed by the formula

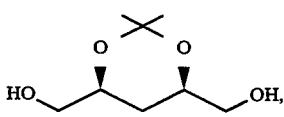

in the presence of a lipase.

5. A process for producing a meso-1,5-dialkanoyloxy-2,4-dihydroxypentane expressed by the formula

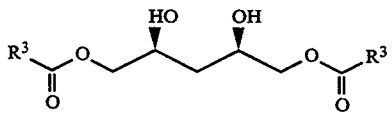  (3)

wherein $R^3$ represents an alkyl group of 1 to 10 carbon atoms, which process comprises reacting an ester with meso-1,2,4,5-pentanetetraol expressed by the formula

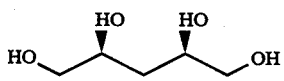  (2)

in the presence of a lipase.

6. A process for producing an optically active erythro-3,5-O-isopropylidene; 3,5,6-trihydroxy-hexanoate, which process comprises reacting an ester with meso-1,2,4,5-pentanetetraol expressed by the formula

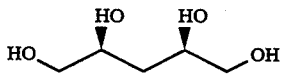  (2)

in the presence of a lipase to prepare a meso-1,5-alkanoyloxy-2,4-dihydroxypentane expressed by the formula

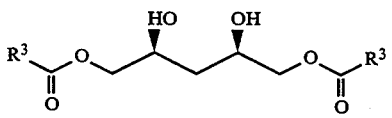  (3)

wherein $R^3$ represents an alkyl group of 1 to 10 carbon atoms; ketalizing the compound (3) to prepare a meso-1,5-dialkanoyloxy-2,4-O-isopropylidene-2,4-dihydroxypentane expressed by the formula

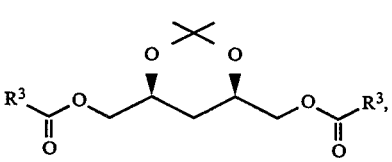  (4)

dealkanolizing the compound (4) to prepare meso-2,4-O-isopropylidene-1,2,4,5-pentane tetraol expressed by the formula

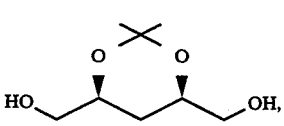  (5)

reacting an ester with (5) in the presence of a lipase to prepare an optically active erythro-1-alkanoyloxy-2,4-O-isopropylidene-1,2,5-pentanetriol expressed by the formula

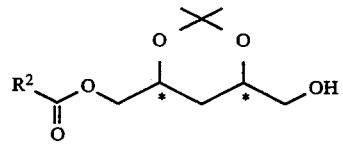  (6)

wherein $R^2$ represents an alkyl group of 1 to 6 carbon atoms, halogenating it, to prepare an optically active alkanoyloxy-2,4-O-isopropylidene-2,4-dihydroxy-5-halogenopentane expressed by the formula

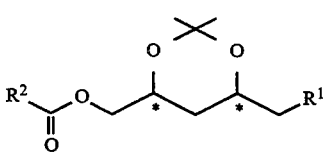  (1-1)

wherein $R^1$ represents a halogen atom and $R^2$ represents an alkyl group of 1 to 6 carbon atoms, and cyanizing it, to prepare an optically activate erythro-1-alkanoyloxy-2,4-O-isopropylidene-2,4-dihydroxy-5-cyanopentane expressed by the formula

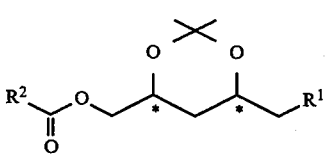  (1-2)

wherein $R^1$ represents a cyano group and $R^2$ represents an alkyl group of 1 to 6 carbon atoms, and converting the cyano group into an alkoxycarbonyl group, to prepare an optically active erythro-3,5-O-isopropylidene-3,5,6-trihydroxyhexanoate expressed by the formula

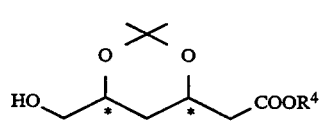  (1-3)

wherein $R^4$ represents an alkyl group of 1 to 6 carbon atoms.

DETAILED DESCRIPTION OF PREFERRED EMBODIMENTS

A compound of the formula (1) of the present invention wherein $R^1$ represents a cyano group has an alkanoyloxy group at the 1-position and a cyano group at the 5-position in the molecule. The cyano group at the 5-position is equivalent to a carboxyl group in the aspect of organosynthetic chemistry; hence if required, the cyano group can be easily converted into a carboxyl group according to a conventional organochemical method. Further, the alkanoyloxy group can be easily converted into a hydroxyl group under mild conditions i.e. by treating it with calcium carbonate, sodium carbonate or the like in an alcohol, and this hydroxyl group can be further converted into a cyano group under similar mild conditions as shown in the examples, the fifth step and the sixth step mentioned below.

In short, the compound of the formula (1) of the present invention can be regarded as equivalent to the optically active nitrile compound (10) which is a raw material for preparing the pyrrole derivative (7) as one of the HMG-CoA reductase inhibitors, or regarded as a compound which can be easily converted into (10). Further, as shown in the Examples, it is possible to prepare (1) which is stereochemically a (2S,4S) substance, in a superior optical purity, according to the method of the present invention, and this is a preferable steric substance as a raw material for preparing the pyrrole derivative (7) having a physiological activity.

Among the compounds of formula (1) of the present invention, a compound of formula (1) wherein $R^1$ represents a halogen atom is prepared via five steps starting from meso-1,2,4,5-pentanetetraol (2), while a compound of the formula (1) wherein $R^1$ represents a cyano group is prepared via six steps.

(First step) Preparation of meso-1,5-dialkanoyloxy-2,4-dihydroxypentane (3)

The first reaction step is carried out by agitating a mixture of meso-1,2,4,5-pentanetetraol (2), a lipase and an ester to subject only hydroxyl groups at the 1 and 5 positions to ester exchange. In this case, the ester exchange reaction advances only at the primary hydroxyl groups and selective esterification can be effected only at the 1, 5 positions. As to the usable lipase, any kinds are usable as far as they can selectively esterify only the primary hydroxyl groups.

As to the lipase usable in this case, commercially available ones may be sufficient, for example, Lipase AP (origin: *Aspergillus nigar*, made by Amano Pharmaceutical Co. Ltd.), Lipase M (origin: *Mucor javanicus*, made by Amano Pharmaceutical Co. Ltd.), Lipase P (origin: Pseudomonas species, made by Amano Pharmaceutical Co.,Ltd.), Lipase PS (origin: *Pseudomonas species*, made by Amano Pharmaceutical Co. Ltd.),Lipase CES (origin: *Pseudomonas species*, made by Amano Pharmaceutical Co. Ltd.), Lipase CE (origin: *Humicola lanuginosa*, made by Amano Seiyaku Co., Ltd.), Lipase II (origin: porcin pancreas, made by Cygma Co., Ltd.), Lipase VIII (origin: *Geotrichumu candidom*, made by Cigma Co., Ltd.), Lipase X (origin: *Rhizopus delemar*, made by Cigma Co., Ltd.), Lipase (origin: *Chromobacterium viscosum*, made by Toyo Jozo Co., Ltd.), Palatase A (origin: *Aspergillus nigar*, made by Novo Industry, Co., Ltd.), Lipase (origin: *Rhizopus nivenus*, supplied by Nagase Sangyo Co., Ltd.) and lipase B (origin: *Pseudomonas fragi*, made by Sapporo Beer Co., Ltd.).

The quantity of the ester used may be 2 to 3 molar equivalents to (2). However, since the reaction rate of the ester exchange reaction at the primary hydroxyl group is far higher than that at the secondary hydroxyl group, a large excess quantity of the ester may be used.

Examples of the ester used are alkyl carboxylates such as alkyl acetates, alkyl propionates, alkyl butanoates, alkyl pentanoates, alkyl hexanoates, alkyl heptanoates, vinyl esters such as vinyl acetate, vinyl propionate, vinyl butanoate, vinyl pentanoate, vinyl hexanoate, vinyl heptanoate, vinyl laurate, etc., triglycerides such as triacetin, tributyrin, tricaproin, etc.

In this case, since the steric selectivity is not influenced by the alkyl chain length, it is also possible to use any chain length ester. A reaction-solvent is not always required, but since the solubility of (2) in the ester is low, it is preferred to use a co-solvent such as dimethylformamide at an appropriate time.

Withdrawal of the objective substance (3) from the reaction system after completion of the reaction can he easily carried out as follows:

Namely, when the lipase in a suspension state is filtered off and the filtrate is concentrated, a raw substance (3) is obtained. This material is usable for the subsequent reaction without purification. Further, the lipase filtered off can he reused as it is. For the reaction temperature, room temperature is sufficient. The reaction time is 1 to 50 hours.

(Second step) Preparation of meso-1,5-dialkanoyloxy-2,4-O-isopropylidene-2,4-dihydroxypentane (4)

The second reaction step is carried out by reacting acetone or 2,2-dimethoxypropane with meso-1,5-dialkanoyloxy-2,4-dihydroxypentane (3) in the presence of an acid catalyst. As the acid catalyst, mineral acids such as sulfuric acid, hydrochloric acid, etc., sulfonic acids such as p-toluenesulfonic acid, camphor-sulfonic acid, etc., and an acidic ion exchange resin are preferably used. As the reaction temperature, those temperature in the vicinity of room temperature are preferred. The reaction can be carried out in the absence of solvent, but if the solubility of (3) is low, it is preferred to carry out the reaction by adding dimethylformamide at an appropriate time.

(Third step) Preparation of meso-2,4-isopropylidene-1,2,4,5-pentanetetraol (5)

The third reaction step is carried out by deacetylating meso-1,5-dialkanoyloxy-2,4-O-isopropylidene-2,4-dihydroxypentane (4) under a neutral or basic condition. For example, the reaction is carried out by reacting therewith sodium carbonate, potassium carbonate, calcium carbonate, barium carbonate, potassium hydroxide, sodium hydroxide, calcium hydroxide, barium hydroxide or the like in a polar solvent such as methanol, ethanol, isopropanol, water or the like.

Further, it is also possible to dealkanoylize it in a reducing manner, by reacting a reducing agent such as lithium aluminum hydride, lithium boron hydride, sodium boron hydride or the like in a solvent such as diethyl ether, tetrahydrofuran or the like.

(Fourth step) Preparation of optically active erythro-1-alkanoyloxy-2,4-O-isopropylidene-1,2,5-pentanetriol (6)

The fourth reaction step is carried out by agitating a mixture of meso-2,4-O-isopropylidene-1,2,4,5-pentanetetraol (5), a lipase and an ester to subject only one of hydroxyl groups at the 1 and 5 positions to ester exchange. In this case, the ester exchange reaction advances stereoselectively to obtain the optically active (6). As to the lipase used, any kinds may be used as far as only one of the hydroxyl groups at 1 and 5 positions can be stereoselectively esterified.

For the lipase used in this case, commercially available lipases are sufficient. Examples thereof have been mentioned in the above first step. Among these, lipases of Pseudomonas genus origin are particularly preferred.

The quantity of the ester used may be 1 to 2 molar equivalents based upon (5), but since the stereoselectivity of the ester exchange reaction is high, the ester may be used in a large excess quantity. As the ester used, alkyl carboxylates such as alkyl acetates, alkyl propionates, alkyl butanoates, alkyl pentanoates, alkyl hexanoates, alkyl heptanoates, vinyl esters such as vinyl acetate, vinyl propionate, vinyl butanoate, vinyl pentanoate, vinyl hexanoate, vinyl heptanoate, triglycerides such as triacetin, tributyrin, tricaproin, are preferably used.

Since the stereoselectivity is not influenced by the alkyl chain length, it is also possible to use any chain length ester. The reaction solvent is not always required, but when the solubility of (5) in the ester is low, it is preferred to use a co-solvent such as dimethylformamide at an appropriate time. Withdrawal of the objective substance (6) from the reaction system after completion of the reaction can be easily carried out as follows:

Namely, by filtering off the lipase in a suspended state and then concentrating the filtrate, the objective compound (6) is obtained. Further, the lipase filtered off can be reused as it is. For the reaction temperature, room temperature may be sufficient. The reaction time is 0.5 to 50 hours.

(Fifth step) Preparation of optically active erythro-1-alkanoyloxy-2,4-O-isopropylidene-2,4-dihydroxy-5-halogenopentane (a compound of the formula (1) wherein $R^1$ represents a halogen atom)

The fifth reaction step is carried out by halogenating the optically active erythro-1-alkanoyloxy-2,4-O-isopropylidene-1,2,5-pentanetriol (6) in a neutral or basic condition. For example, it is possible to prepare a chloride (a compound of the formula (1) wherein $R^1$ represents a chlorine atom) by heating (6) under reflux in carbon tetrachloride in the presence of triphenylphosphine or treating (6) with N-chlorosuccinic acid imide in dichloromethane in the presence of triphenylphosphine.

Further, it is possible to prepare a bromide (a compound of the formula (1) wherein $R^1$ represents a bromine atom) by reacting one equivalent or more of N-bromosuccinic acid imide or 2 to 3 equivalents of carbon tetrabromide with (6) in dichloromethane in the presence of one equivalent of triphenylphosphine. Further, it is possible to prepare an iodide (a compound of the formula (1) wherein $R^1$ represents an iodine atom), by reacting triphenylphosphine and iodine with (6) in the presence of imidazole. The iodide can also be prepared by treating the chloride or bromide with sodium iodide in acetone.

(Sixth step) Preparation of an optically active erythro-1-alkanoyloxy-2,4-O-isopropylidene-2,4-dihydroxy-5-cyanopentane (a compound of the formula (1) wherein $R^1$ represents a cyano group)

The sixth reaction sixth step is carried out by reacting sodium cyanide, potassium cyanide or copper cyanide with an optically active erythro-1-alkanoyloxy-2,4-O-isopropylidene-2,4-dihydroxy-5-halogenopentane (a compound of the formula (1) wherein $R^1$ represents a halogen atom) in dimethylformamide or dimethylsulfoxide.

In the case where the optically active erythro-1-alkanoyloxy-2,4-O-isopropylidene-2,4-dihydroxy-5-halogenopentane is an iodide, the reaction proceeds at room temperature, but in the case where it is a chloride or a bromide, heating is required for the reaction.

As to the preparation of meso-1,2,4,5-pentanetetraol (2) as the starting raw material, a preparation method using adonitol as the raw material (Zhuo-Feng XIE et al, Chem. Pharm. Bull., 37, (6), 1650 (1989)), and a preparation method using 1,2-O-isopropylidene-1,2,4-butanetriol as the raw material (Johann Mulzer et al, Liebig's Ann. Chem., 947 (1991)) have been known; hence (2) can be prepared according to such methods.

As to the preparation of optically active erythro-1-alkanoyloxy-2,4-O-isopropylidene-1,2,5-pentanetriol (6), a separate preparation method has been reported by Zhuo-Feng XIE et al (Zhuo-Feng XIE et al, Chem. Pharm. Bull., 37 (6), 1650 (1989)). (6) is prepared by selective protection of hydroxyl groups at the 1 and 5 positions of meso-1,2,4,5-pentanetetraol and protection of the 2 and 4 positions with acetonide and succeeding asymmetric hydrolysis of the resulting diacetate with a lipase. However, as to the selectivity of the selective protection of hydroxyl groups at the 1 and 5 positions with an acetyl group using acetic anhydride, the yield is as low as 61%. Whereas, the yield of the compound having hydroxyl groups at 1 and 5 positions protected with the alkanoyloxy group in the present invention was 75%.

Further, the optically active erythro-1-alkanoyloxy-2,4-O-isopropylidene-1,2,5-pentatriol obtained by the asymmetric hydrolysis with a lipase has a stereochemical structure of (2R,4R), that is, an antipode to the compound sought; hence the above method is not a commercially useful method.

Further, it is necessary to carry out assymetric hydrolysis with a lipase in water, but since the substrate is not water-soluble, a large quantity of reaction solvent is required. Further, recovery of lipase from water and its reuse are impossible. (Effectiveness of the Invention)

The novel compound of the present invention, optically active erythro-1-alkanoyloxy-2,4-O-isopropylidene-2,4-dihydroxy-5-substituted pentane (1), is an equivalent compound to an optically active nitrile compound (10) which is a raw material for preparing a pyrrole derivative (7) as one of HMG-CoA reductase inhibitors, or a compound which can be easily converted into (10).

Further, the novel compound of the present invention, optically active erythro-1-alkanoyloxy-2,4-O-isopropylidene-2,4-dihydroxy-5-substituted pentane (1) can be preferably used not only for the above optically active nitrile compound (10) which is a raw material for preparing a pyrrole derivative (7) as one of HMG-CoA reductase inhibitors, but also for a raw material for preparing physiologically active compounds as mentioned below. Examples thereof are as follows:

The novel compound of the present invention, optically active erythro-1-alkanoyloxy-2,4-O-isopropylidene-2,4-dihydroxy-5-cyanopentane (a compound of the formula (1) wherein $R^1$ represents cyano group) is easily lactonized by hydrolysis of the cyano group, followed by acid treatment, to afford a lactone (22).

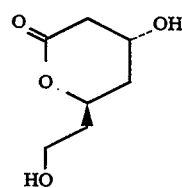

This product can afford the lactone site of Compactin (Formula 23) known as one of HMG-CoA reductase inhibitors (A. G. Brown et al, J. Chem. Soc. Perkin Trans. I, 1165 (1976)) or that of mevinolin (Formula 24) similarly known thereas (A. W. Alberts et al, Proc. Natn. Acad. Sci. U.S.A. 77, 3957 (1980)).

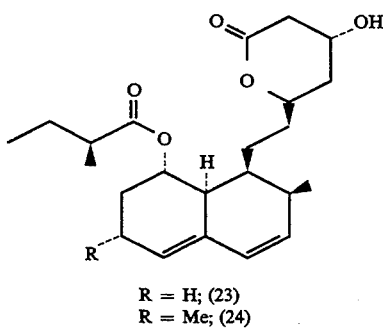

R = H; (23)
R = Me; (24)

Further, the novel compound of the present invention, optically active erythro-1-alkanoyloxy-2,4-O-isopropylidene-2,4-dihydroxy-5-cyanopentane (a compound of the formula (1) wherein $R^1$ represents cyano group), is also useful as a raw material for preparing a pyridine derivative (Formula 25) (Eur. Pat. Appl., EP 356778) which is also an HMG-CoA reductase inhibitor.

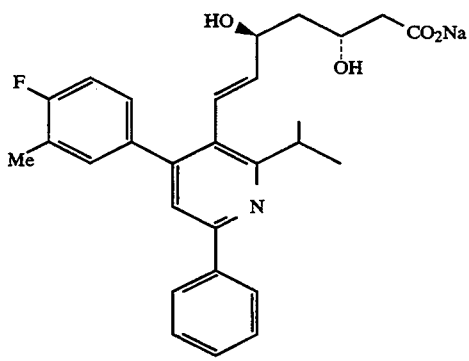

Namely, an aldehyde (formula (26)) is prepared by removal of the protective alkanoyloxyl group from the 1-position and oxidation, followed by introduction of a pyridine core, hydrolysis, removal of acetonide and conversion of the ester site into a metal salt to prepare (25).

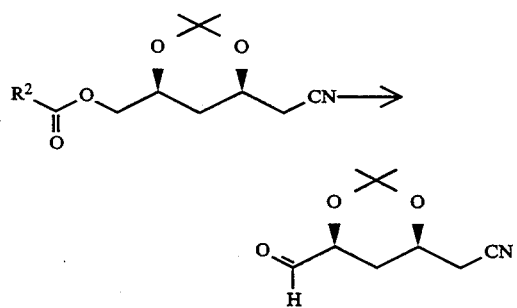

Further, in the present invention, such useful novel optically active compounds can be prepared in a simple manner. Next, the effectiveness of the procedure of the present invention will be enumerated.

① The esterification at the first step has a high regionselectivity; hence only the primary hydroxyl group can be esterified without employing any particular condition.

② The esterification with a lipase at the first and third steps can be carried out in an organic solvent; hence in spite of an enzymatic reaction, the reaction can be carried out in a high substrate concentration.

③ The esterification with a lipase at the first and third steps can be carried out in an organic solvent; hence the recovery of the lipase after used and its reuse are easy.

④ The esterification with a lipase at the fourth step has a high stereoselectivity; hence it is possible to obtain an optically pure compound by a once enzymatic reaction.

⑤ The reaction conditions at the respective steps are very mild. The reactions at any steps except for the sixth step are all carried out at room temperature.

⑥ The yields at the respective steps are high (1st. step: 75%, 2nd. step: 63%, 3rd. step: quantitative, 4th step: 70%, 5th step: 77%, 6th step: 55% and the total yield: 14%).

EXAMPLES

The present invention will be described in more detail by way of representative examples.

EXAMPLE 1

(First step)
Preparation of meso-1,5-diacetoxy-2,4-dihydroxy-pentane (3)

A mixture of meso-1,2,4,5-pentanetetraol (2) (25.7 g, 0.19 mol), Lipase PS (made by Amano Pharmaceutical Co., Ltd.) (9 g), vinyl acetate (48.7g, 0.57 mol) and dimethylformamide (DMF) (40 ml) was agitated at room temperature for 28 hours.

The Lipase PS was filtered off, followed by washing the filtration residue with ethyl acetate (50 ml), combining the filtrate with ethyl acetate used for the washing, and concentrating the mixture under reduced pressure to obtain as a residue an, orange colored, oily meso-1,5-diacetoxy-2,4-dihydroxypentane (3) (25.2 g, yield: 75%). This product was used as a raw material for the second step without purification.

( Second step )
Preparation of meso-1,5-diacetoxy-2,4-O-isopropylidene-2,4-dihydroxypentane (4)

p-Toluenesulfonic acid monohydrate (2.5 g, 0.013 mol) was added to a mixture of meso-1,5-diacetoxy-2,4-dihydroxypentane (3) (25.2 g, 0.14 mol) obtained at the first step, 2,2-dimethoxypropane (400 ml) and DMF (200 ml), under ice cooling, followed by agitating the resulting mixture at room temperature for 22 hours.

Sodium hydrogen carbonate (20 g) was added under ice cooling, followed by agitating the mixture for one hour, adding a saturated aqueous solution of sodium hydrogen carbonate (300 ml), extracting the mixture with ethyl acetate (300 ml), twice washing the organic layer with water (200 ml) and drying over anhydrous magnesium sulfate.

Ethyl acetate was distilled off under reduced pressure, followed by subjecting the residue to silica gel column chromatography (eluent: toluene-ethyl acetate (8:1), Rf value: 2.0), to obtain a raw meso-1,5-diacetoxy-2,4-O-isopropylidene-2,4-dihydroxypentane (4) in the form of a yellow oily substance.

This substance was recrystallized from n-heptane(100ml) to obtain meso-1,5-diacetoxy-2,4-O-isopropylidene-2,4-dihydroxypentane (4) (22.8 g, yield: 63%) in the form of colorless needles).

M. P.: 50.7°–53.5° C.

¹H-NMR (90 MHz, CDCl₃) δ(ppm): 1.36–1.68 (3H, m), 1.43 (3H, s), 1.46 (3H, s), 2.09 (6H, s), 4.01–4.21 (6H, m) ¹³C-NMR (90 MHz, CDCl₃) δ(ppm): 19.5, 20.5, 29.0, 29.5, 67.5, 99.5, 171.0 MS m/z: 245 (M⁺-15), 203, 187

(Third step) Preparation of meso-2,4-O-isopropylidene-1,2,4,5-pentanetetraol (5)

A mixture of meso-1,5-diacetoxy-2,4-O-isopropylidene-2,4-dihydroxypentane (4) (15.2 g, 0.6 mol) obtained at the second step with THF (250 ml) was dropwise to a suspension of lithium aluminum hydride (4.6 g, 0.12 mol) and THF (125 ml) at 0° C. or lower, followed by agitating the mixture at room temperature for 2 hours, adding ethyl acetate (25 ml), water (25 ml) and a 2N aqueous solution of NaOH (5 ml) in this order, and agitating the mixture at room temperature for 30 minutes.

The deposited crystals were filtered off, followed by washing the filtration residue with THF (100 ml), combining the filtrate and THF used for the washing, concentrating the mixture under reduced pressure and subjecting the residue according to silica gel column chromatography (eluent, toluene: ethyl acetate (2:1) to obtain colorless, oily meso-2,4-O-isopropylidene-1,2,4,5-pentanetetraol (5) (11.5 g, yield: quantitative).

¹H-NMR (90 MHz, CDCl₃) δ(ppm): 1.3–1.59 (3H, m), 1.43 (3H, s), 1.47 (3H, s), 3.40 (2H, brs), 3.62 (4H, m), 4.00–4.20 (4H, m)

(Fourth step) Preparation of (2R, 4S)-erythro-1-acetyloxy-2,4-O-isopropylidene-1,2,5-pentanetriol (6)

A mixture of meso-2,4-O-isopropylidene-1,2,4,5-pentanetetraol (5) (8.2 g, 4.6 mmol) obtained at the third step, vinyl acetate (100 ml) and Lipase PS (made by Amano Pharmaceutical Co. Ltd. )(1 g) was agitated at room temperature for one hour and 35 minutes, followed by filtering off the Lipase PS, washing the filtration residue with ethyl acetate (10 ml), combining the filtrate with ethyl acetate used for the washing and concentrating the mixture under reduced pressure.

The residue was subjected to silica gel column chromatography (eluent, toluene: ethyl acetate (2:1), Rf value: 2.3) to obtain colorless, oily (2R,4S)-erythro-1-acetyloxy-2,4-O-isorpopylidene-1,2,5-pentanetriol (6) (7.1 g, yield: 70%).

$[\alpha]$ D²⁷+4.7° (2.56, CHCl₃) ¹H-NMR (90 MHz, CDCl₃) δ(ppm): 1.3–1.55 (2H, m), 1.43 (3H, s), 1.47 (3H, s), 2.08 (3H, s), 3. 40 (1H,brs), 3. 65 (2H, m), 3. 97–4.20 (4H, m)

The optical purity of the thus obtained (2R,4S)-erythro-1-acetyloxy-2,4-O-isopropylidene-1,2,5-pentanetriol (6) was determined by deriving the (6) into MTPA (α-methoxy-α-(trifluoromethyl) phenylacetic acid) ester and subjecting it to 400 MHz-¹H-NMR analysis as follows:

Namely, a mixture of (2R,4S)-erythro-1-acetyloxy-2,4-O-isopropylidene-1,2,5-pentanetriol (6) (115 mg, 0.53 mmol), R-α-methoxy-α-(trifluoromethyl)phenylacetic acid chloride (199 mg, 0.79 mmol) and pyridine (3 ml) was agitated at room temperature for 12 hours.

Water was added to the resulting material, followed by extracting with toluene, washing the organic layer with a saturated aqueous solution of sodium carbonate and then with water, drying over anhydrous magnesium sulfate, filtering off the anhydrous magnesium sulfate, distilling off the solvent under reduced pressure and subjecting the residue to silica gel column chromatography (eluent, toluene: ethyl acetate (3/1) to obtain a colorless, oily MTPA ester (250 mg). The peak of 3.56 ppm observed by NMR analysis was a single peak; thus, (6) has been found to be chemically pure.

¹ H-NMR (400 MHz, CDCl₃) δ(ppm): 1.29–1.32 (2H, m), 1.40 (3H, s), 1.42 (3H, s), 3.56 (3H, s), 4.02–4.35 (6H, m), 7.40–7.57 (5H, m)

(Fifth step) Preparation of (2R,4S)-erythro-1-acetyloxy-2,4-O-isopropylidene-2,4-dihydroxy-5-bromopentane (a compound of the formula (1) wherein R¹ represents bromine atom)

To a mixture of (2R,4S)-erythro-1-acetyloxy-2,4-O-isopropylidene-1,2,5-pentanetriol (6) (5.4 g, 0.025 mol) obtained at the fourth step with dichloromethane (100 ml) were fed triphenylphosphine (7.8 g, 0.029 mol) and carbon tetrabromide (12.3 g, 0.037 mol) in that order, followed by agitating the mixture at room temperature for one hour, adding a saturated aqueous solution of sodium carbonate (2 ml), agitating for 30 minutes, and drying over anhydrous magnesium sulfate.

The solids were filtered off, followed by washing the filtration residue with dichloromethane (20 ml), concentrating the resulting dichloromethane under reduced pressure and subjecting the residue to silica gel column chromatography (eluent, toluene: ethyl acetate (3:1)) to obtain a colorless, oily (2R,4S)-erythro-1-acetyloxy-2,4-O-isopropylidene-2,4-dihydroxy-5-bromopentane (a compound of the formula (1) wherein R¹ represents bromine atom) (5.4 g, yield: 77%).

¹H-NMR (90 MHz, CDCl₃) δ(ppm) :1.3–1.57 (2H, m), 1.44 (3H, s), 1.48 (3H, s), 2.10 (3H, s), 3.45 (2H, q), 3.97–4.29 (4H, m)

(Sixth step) Preparation of (2S,4S)-erythro-1-acetyloxy-2,4-O-isopropylidene-2,4-dihydroxy-5-cyanopentane (a compound of the formula (1) wherein R¹ represents cyano group)

A mixture of (2R, 4S)-erythro-1-acetyloxy-2,4-O-propylidene-2,4-dihydroxy-5-bromopentane (a compound of the formula (1) wherein R¹ represents a bromine atom) (4.8 g, 0.017 mol) obtained at the fifth step, DMF (50 ml) and sodium cyanide (1.7 g, 0.034 mol) was agitated at about 70° C. for one hour, followed by allowing the resulting material to cool, adding water (50 ml) and extracting with ethyl acetate (50 ml).

The organic layer was twice washed with water (50 ml), followed by drying over anhydrous magnesium sulfate, filtering off anhydrous magnesium sulfate, concentrating ethyl acetate under reduced pressure, and subjecting the residue to silica gel column chromatography (eluent, toluene: ethyl acetate (5:1)), to obtain slightly yellow, oily (2S, 4S)-erythro-1-acetyloxy-2,4-O-isopropylidene-2,4-dihydroxy-5-cyanopentane (a compound of the formula (1) wherein R¹ represents cyano group) (2.1 g, yield: 55%).

¹H-NMR (400 MHz, CDCl₃) δ(ppm): 1.33–1.43 (2H, m), 1.42 (3H, s), 1.46 (3H, s), 2.09 (3H, s), 2.50 (2H, q), 3.97.–4.25 (4H, m) ¹³C-NMR (90 MHz, CDCl₃) δ(ppm): 19.4, 20.7, 24.8, 29.5, 32.0, 64.6, 66.5, 66.6, 99.3, 116.5, 170.6

EXAMPLE 2

(application example)

Preparation of (2R,4S)-erythro-3,5-O-isopropylidene-3,5,6-trihydroxyhexanoate (1-3)

To a mixture of (2S,4S)-erythro-1-acetyloxy-2,4-O-isopropylidene-2,4-dihydroxy-5-cyanopentane (a compound of the formula(1) wherein R¹ represents cyano group) (2.0 g, 7.9 mmol) and dichloromethane (20 ml), a 1.0M solution of diisobutyl aluminium hydride in toluene (24ml) was added dropwise at −70° C., and the mixture was stirred for 20 min.

After adding methanol (5 ml), a saturated aqueous solution of ammonium chloride (5 ml) and diethyl ether (5 ml), the resulting precipitate was filtered off, followed by concentrating the filtrate under reduced pressure to obtain (2R, 4S)-erythro-3,5-O-iso propylidene-3,5,6-trihydroxyhexanal (2.0 g).

A mixture of the aldehyde (2.0 g, 7.8 mmol) obtained above, DMF (100 ml), methanol(1.6 ml) and pyridum dichromate was stirred for 40 min. A saturated aqueous solution of sodium hydrogen carbonate was added under ice cooling, followed by extracting the mixture with ethyl acetate, washing the organic layer with water and drying over anhydrous magnesium sulfate.

Ethyl acetate was distilled off under reduced pressure, followed by subjecting the residue to silica gel column chromatography (eluent: toluene-ethyl acetate (1:1)), to obtain colorless, oily (2R, 4S)-erythro-3,5-O-isopropylidene-3,5,6-trihydroxyhexanoate (1-3) (1.57 g, yield: 70%).

$^1$H-NMR (400 MHz, CDCl$_3$) δ(ppm): 1.29–1.53 (2H,m), 1.39 (3H,s), 1.48 (3H,s), 1.58 (3H, brs), 2.49 (2H,m), 3.56 (2H,m), 3.69 (3H,s), 4.02 (1H,m), 4.34 (1H,m)

What we claim is:

1. A process for producing an optically active erythro-1-alkanoyloxy-2,4-O-isopropylidene-2,4-dihydroxy-5-halogenopentane, which process comprises reacting an ester containing a group R$^3$CO with meso-1,2,4,5-pentanetetraol expressed by the formula

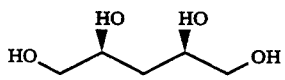 (2)

in the presence of a lipase which catalyzes an ester exchange reaction with primary hydroxyl groups at a rate much greater than secondary alcohol groups to prepare a meso-1,5-alkanoyloxy-2,4-dihydroxypentane expressed by the formula

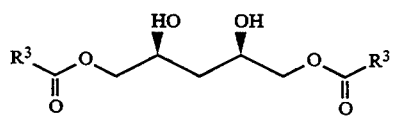 (3)

wherein R$^3$ represents an alkyl group of 1 to 10 carbon atoms;

ketalizing the compound (3) to prepare a meso-1,5-dialkanoyloxy-2,4-O-isopropylidene-2,4-dihydroxypentane expressed by the formula

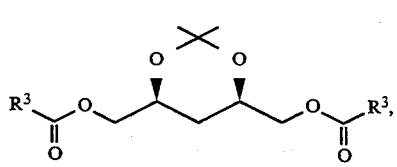 (4)

dealkanolizing the compound (4) to prepare meso-2,4-O-isopropylidene-1,2,4,5-pentane tetraol expressed by the formula

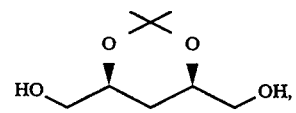 (5)

reacting an ester containing a group R$^2$CO with (5) in the presence of a lipase which catalyzes an ester exchange reaction with only one of the hydroxyl groups at the 1 and 5 positions of compound (5) to prepare an optically active erythro-1-alkanoyloxy-2,4-O-isopropylidene-1,2,5-pentanetriol expressed by the formula

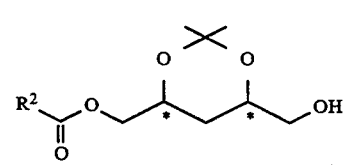 (6)

wherein R$^2$ represents an alkyl group of 1 to 6 carbon atoms, and halogenating compound (6) to prepare an optically active erythro-1-alkanoyloxy-2,4-O-isopropylidene-2,4-dihydroxy-5-halogenopentane expressed by the formula

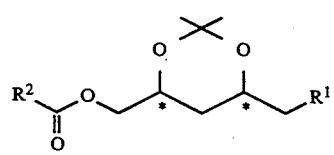 (1-1)

wherein R$^1$ represents a halogen atom and R$^2$ represents an alkyl group of 1 to 10 carbon atoms.

2. A process for producing an optically active erythro-1-alkanoyloxy-2,4-O-isopropylidene-2,4-dihydroxy-5-cyanopentane, which process comprises reacting an ester containing a group R$^3$CO with meso-1,2,4,5-pentanetetraol expressed by the formula

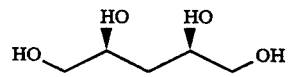 (2)

in the presence of a lipase which catalyzes an ester exchange reaction with primary hydroxyl groups at a rate much greater than secondary alcohol groups to prepare a meso-1,5-alkanoyloxy-2,4-dihydroxypentane expressed by the formula

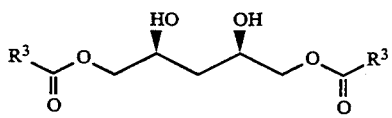 (3)

wherein R$^3$ represents an alkyl group of 1 to 10 carbon atoms;

ketalizing the compound (3) to prepare a meso-1,5-dialkanoyloxy-2,4-O-isopropylidene-2,4-dihydroxypentane expressed by the formula

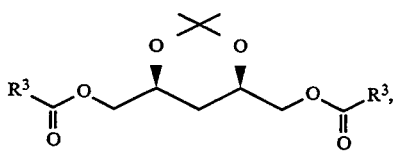
(4)

dealkanolizing the compound (4) to prepare meso-2,4-O-isopropylidene-1,2,4,5-pentane tetraol expressed by the formula

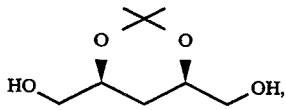
(5)

reacting an ester containing a group R²CO with (5) in the presence of a lipase which catalyzes an ester exchange reaction with only one of the hydroxyl groups at the 1 and 5 positions of compound (5) to prepare an optically active erythro-1-alkanoyloxy-2,4-O-isopropylidene-1,2,5-pentanetriol expressed by the formula

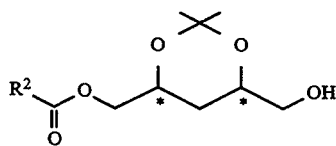
(6)

wherein $R^2$ represents an alkyl group of 1 to 6 carbon atoms, halogenating compound (6) to prepare an optically active alkanoyloxy-2,4-O-isopropylidene-2,4-dihydroxy-5-halogenopentane expressed by the formula

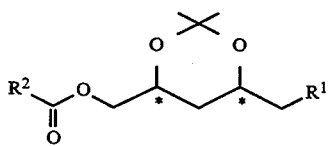
(1-1)

wherein $R^1$ represents a halogen atom and $R^2$ represents an alkyl group of 1 to 6 carbon atoms, and cyanizing compound (1-1) to prepare an optically active erythro-1-alkanoyloxy-2,4-O-isopropylidene-2,4-dihydroxy-5-cyanopentane expressed by the formula

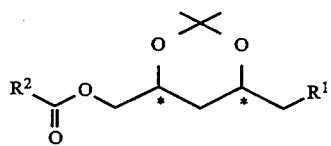
(1-2)

wherein $R^1$ represents a cyano group and $R^2$ represents an alkyl group of 1 to 6 carbon atoms.

3. A process for producing an optically active erythro-1-alkanoyloxy-2,4-O-isopropylidene-1,2,5-pentanetriol expressed by the formula

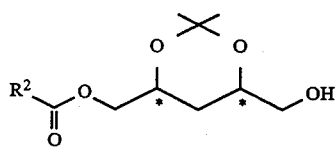
(6)

wherein $R^2$ represents an alkyl group of 1 to 6 carbon atoms, which process comprises reacting an ester having an R²CO group with meso-2,4-O-isopropylidene-1,2,4,5-pentanetetraol expressed by the formula

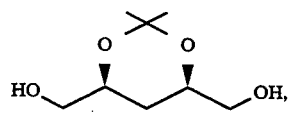
(5)

in the presence of a lipase which catalyzes an ester exchange reaction with only one of the hydroxyl groups at the 1 and 5 positions of compound (5).

4. A process for producing a meso-1,5-dialkanoyloxy-2,4-dihydroxypentane expressed by the formula

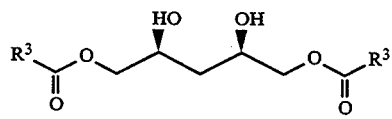
(3)

wherein $R^3$ represents an alkyl group of 1 to 10 carbon atoms, which process comprises reacting an ester having a R³CO group with meso-1,2,4,5-pentanetetraol expressed by the formula

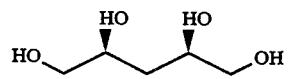
(2)

in the presence of a lipase which catalyzes an ester exchange reaction with primary hydroxyl groups at a rate much greater than secondary alcohol groups.

5. A process for producing an optically active erythro-3,5-O-isopropylidene-3,5,6-trihydroxy-hexanoate, which process comprises reacting an ester having an R³CO group with meso-1,2,4,5-pentanetetraol expressed by the formula

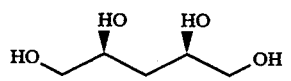
(2)

in the presence of a lipase which catalyzes an ester exchange reaction with primary hydroxyl groups at a rate much greater than secondary alcohol groups to prepare a meso-1,5-alkanoyloxy-2,4-dihydroxypentane expressed by the formula

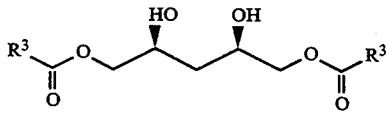
(3)

wherein $r^3$ represents an alkyl group of 1 to 10 carbon atoms;

ketalizing the compound (3) to prepare a meso-1,5-dialkanoyloxy-2,4-O-isopropylidene-2,4-dihydroxypentane expressed by the formula

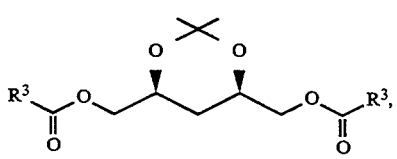
(4)

dealkanolizing the compound (4) to prepare meso-2,4-O-isopropylidene-1,2,4,5-pentane tetraol expressed by the formula

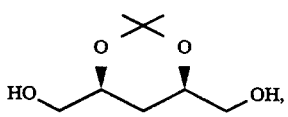
(5)

reacting an ester having an $R_2CO$ group with (5) in the presence of a lipase which catalyzes an ester exchange reaction with only one of the hydroxyl groups at the 1 and 5 positions of compound (5) to prepare an optically active erythro-1-alkanoyloxy-2,4-O-isopropylidene-1,2,5-pentanetriol expressed by the formula

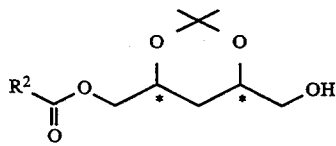
(6)

wherein $R^2$ represents an alkyl group of 1 to 6 carbon atoms, halogenating compound (6) to prepare an optically active alkanoyloxy-2,4-O-isopropylidene-2,4-dihydroxy-5-halogenopentane expressed by the formula

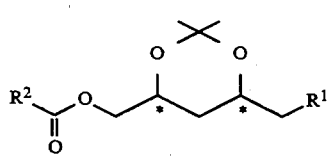
(1-1)

wherein $R^1$ represents a halogen atom and $R^2$ represents an alkyl group of 1 to 6 carbon atoms, and cyanizing compound (1-1) to prepare an optically active erythro-1-alkanoyloxy-2,4-O-isopropylidene-2,4-dihydroxy-5-cyanopentane expressed by the formula

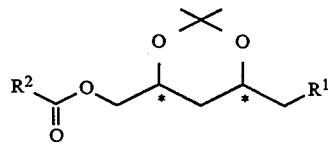
(1-2)

wherein $R^1$ represents a cyano group and $R^2$ represents an alkyl group of 1 to 6 carbon atoms, and converting the cyano group into an alkoxycarbonyl group, to prepare an optically active erythro-3,5-O-isopropylidene-3,5,6-trihydroxyhexanoate expressed by the formula

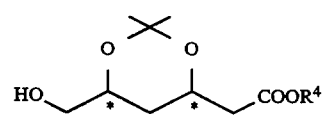
(1-3)

wherein $R^4$ represents an alkyl group of 1 to 6 carbon atoms.

6. A process as claimed in claim 1 wherein ketalizing is conducted with acetone or 2,2-dimethoxypropane in the presence of an acid catalyst.

7. A process as claimed in claim 2 wherein ketalizing is conducted with acetone or 2,2-dimethoxypropane in the presence of an acid catalyst.

8. A process as claimed in claim 5 wherein ketalizing is conducted with acetone or 2,2-dimethoxypropane in the presence of an acid catalyst.

9. A process as claimed in claim 1 wherein the dealkanolizing step is conducted under neutral or basic conditions.

10. A process as claimed in claim 2 wherein the dealkanolizing step is conducted under neutral or basic conditions.

11. A process as claimed in claim 5 wherein the dealkanolizing step is conducted under neutral or basic conditions.

12. A process as claimed in claim 1 wherein the dealkanolizing step is performed with a reducing agent.

13. A process as claimed in claim 2 wherein the dealkanolizing step is performed with a reducing agent.

14. A process as claimed in claim 5 wherein the dealkanolizing step is performed with a reducing agent.

15. A process as claimed in claim 1 wherein halogenation is performed with a tetrahalomethane.

16. A process as claimed in claim 2 wherein halogenation is performed with a tetrahalomethane.

17. A process as claimed in claim 5 wherein halogenation is performed with a tetrahalomethane.

18. A process as claimed in claim 1 wherein halogenation is performed with a halosuccinic acid.

19. A process as claimed in claim 2 wherein halogenation is performed with a halosuccinic acid.

20. A process as claimed in claim 5 wherein halogenation is performed with a halosuccinic acid.

21. A process as claimed in claim 2 wherein cyanizing is performed with a cyanide of sodium, potassium or copper.

22. A process as claimed in claim 5 wherein cyanizing is performed with a cyanide of sodium, potassium or copper.

23. A process as claimed in claim 5 wherein the step of converting comprises forming an aldehyde group from the cyano group with diisobutyl aluminum hydride after which the aldehyde is oxidized to a carboxyl group.

* * * * *

UNITED STATES PATENT AND TRADEMARK OFFICE
CERTIFICATE OF CORRECTION

PATENT NO. : 5,449,793
DATED : September 12, 1995
INVENTOR(S) : Miyazawa et al.

It is certified that error appears in the above-indentified patent and that said Letters Patent is hereby corrected as shown below:

Column 21, Line 1, change "$r^3$" to --$R^3$--;

Signed and Sealed this

Twenty-third Day of July, 1996

Attest:

BRUCE LEHMAN

*Attesting Officer*   *Commissioner of Patents and Trademarks*